US008034623B2

(12) United States Patent
Oh et al.

(10) Patent No.: US 8,034,623 B2
(45) Date of Patent: Oct. 11, 2011

(54) METHOD FOR FREE RADICAL INITIATED PEPTIDE SEQUENCING

(75) Inventors: Han-Bin Oh, Goyang (KR); Bong-Jin Moon, Seoul (KR); Min-hyuck Kang, Seoul (KR); Min-Hee Lee, Suwon (KR)

(73) Assignee: University-Industry Cooperation Foundation, Sogang University, Seoul (KR)

( * ) Notice: Subject to any disclaimer, the term of this patent is extended or adjusted under 35 U.S.C. 154(b) by 0 days.

(21) Appl. No.: 12/579,289

(22) Filed: Oct. 14, 2009

(65) Prior Publication Data

US 2010/0240139 A1 Sep. 23, 2010

(30) Foreign Application Priority Data

Jan. 12, 2009 (KR) .................. 10-2009-0002440

(51) Int. Cl.
*G01N 33/00* (2006.01)

(52) U.S. Cl. .................................. 436/89; 546/208

(58) Field of Classification Search .............. None
See application file for complete search history.

(56) References Cited

U.S. PATENT DOCUMENTS

2007/0087447 A1* 4/2007 Beauchamp et al. ......... 436/173

OTHER PUBLICATIONS

Lee, M. et al. "Gas-phase peptide sequencing by TEMPO-mediated radical generation," Analyst 2009, 134, 1706-1712; available online Jun. 12, 2009.*
Hodyss, R. et al. "Bioconjugates for Tunable Peptide Fragmentation: Free Radical Initiated Peptide Sequencing (FRIPS)," J. Am. Chem. Soc. 2005, 127, 12436-12437.*
Hawker, C. J. "Initiating Systems for Nitroxide-Mediated "Living" Free Radical Polymerizations: Synthesis and Evaluation," Macromolecules 1996, 29, 5248-5254.*

* cited by examiner

*Primary Examiner* — Yelena G Gakh
*Assistant Examiner* — Michelle Adams
(74) *Attorney, Agent, or Firm* — Edwards Angell Palmer & Dodge LLP; Kongsik Kim

(57) ABSTRACT

The present invention relates to a free radical initiator and a method for peptide sequencing using the same. Compared with diazo or peroxy functionalized precursors, the precursors using the present compounds are chemically more robust and can generate radical species by homolytic cleavage upon thermal activation, enabling sequencing of a wider variety of peptides. In addition, the present invention makes it feasible to sequence peptides carrying disulfide bonds.

8 Claims, 9 Drawing Sheets

METHOD FOR FREE RADICAL INITIATED PEPTIDE SEQUENCING

CROSS-REFERENCE TO RELATED APPLICATIONS

This application claims priority from Korean Patent Application No. 2009-0002440, filed on Jan. 12, 2009, in the Korean Intellectual Property Office, the disclosure of which is incorporated herein by reference.

BACKGROUND

1. Technical Field

The present invention relates to a free radical initiator and a method for peptide sequencing using the same.

2. Background Art

Mass spectrometry has played a major role in opening up the new field of proteomics. Identification and characterization of a collection of proteins generally rely on gas-phase sequencing of peptides prepared by enzymatic proteolysis of proteins. Collisionally activated dissociation (CAD) of peptides has been the most widely used tool for sequencing. In recent years, electron capture dissociation (ECD) and electron transfer dissociation (ETD) have received extensive attention as an alternative tool, particularly useful for characterization of posttranslational modifications (PTMs) of proteins as well as for routine peptide analysis.

Top-down analysis of intact proteins by ECD is particularly appealing due to its promising capability for thorough survey of PTMs. In both ECD and ETD, odd-electron radical cation peptide species are prepared as a precursor to peptide backbone dissociations. In ECD and ETD, radical peptide species are formed by capturing an electron provided from a separate e-source or through collisions with anion species, respectively. Peptide backbone cleavage products in ECD/ETD are characterized with c/z ions as major products as well as with a/x ions as minor products, while b and y are main products of collision-based dissociation methods including CAD.

Alternatively, collisional activation of transition metal-peptide complexes has been shown to induce radical cation species. The subsequent collisional activation of the generated radical species followed ECD/ETD-like peptide dissociation pathways, giving rise to a, c, x, and z ions. Laskin et al. showed that charge-remote radical-driven fragmentation pathways are responsible for this type of peptide backbone dissociation (*Anal. Chem.* 2007, 79, 6607). Hydrogen abstraction by the radical site was suggested to initiate the subsequent backbone cleavages, which is also relevant to other odd-electron involving dissociation methods like ECD and ETD.

Another approach to introduce radical species is to attach a free radical initiator to peptide itself. Porter et al. converted N-terminal amines of lysine side chains to peroxycarbamates (*J. Am. Chem. Soc.* 2004, 126, 720; *Med. Chem.* 2006, 14, 6213; *J. Am. Soc. Mass Spectrom.* 2007, 18, 807). Collisional activation of peroxycarbamate peptide adducts complexed with Li, Na, K, or Ag ion gave rise to the neutral loss of the N-terminal side chain, i.e., radical species. Further fragmentation of the generated radical species showed an m/z shift of the b-ions corresponding to the loss of the N-terminal side chain. This shift labelled the b-ion series, which is useful for de novo analysis of peptides with the aid of SALSA algorithm. The Beauchamp group also investigated the use of free radical reactions as a tool for peptide and protein structure determination (*J. Am. Chem. Soc.* 2005, 127, 12436). They conjugated the water-soluble free radical initiator Vazo 68 to the N-terminus of a peptide. The MS/MS of the doubly protonated Vazo 68 conjugated peptides led to a free radical species generated by cleavage at the azo carbon. The product mass spectrum obtained by the subsequent CAD on the radical species showed a number of fragment ions, including many a and z ions, which are the signatures of odd-electron radical-driven fragmentation pathway. This approach was referred to as free radical initiated peptide sequencing (FRIPS).

In this patent application, we expand this FRIPS approach by employing a so-called 'persistent radical' precursor to the N-terminus amino groups or N-terminal amines of lysine side chains. The employed persistent radical species is 'TEMPO (2,2,6,6-Tetramethylpiperidine-1-oxyl)' which is a stable radical widely used as a free radical initiator in polymer chemistry as well as a structural probe in electron spin resonance spectroscopy (Scheme 1).

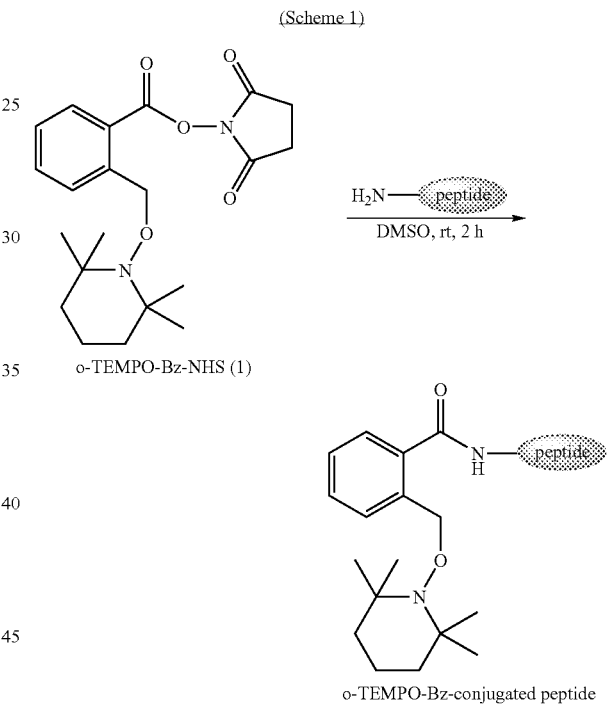

Compared with diazo or peroxy functionalized precursors, a TEMPO-based precursor of the present invention is chemically more robust and can generate radical species by homolytic cleavage upon thermal activation. In addition, the position of the radical site can be easily designated by placing a TEMPO group at the point of interest around the benzyl ring (see the molecular structure of 1 in Scheme 1).

The above information disclosed in this Background section is only for enhancement of understanding of the background of the invention and therefore it may contain information that does not form the prior art that is already known in this country to a person of ordinary skill in the art.

Throughout this application, several patents and publications are referenced and citations are provided in parentheses. The disclosure of these patents and publications is incorporated into this application in order to more fully describe this invention and the state of the art to which this invention pertains.

SUMMARY

The present inventors have expand the FRIPS (free radical initiated peptide sequencing) approach by conjugating the N-terminus amino groups or N-terminal amines of lysine side chains to TEMPO-based precursors, providing compounds capable of generating radical species in more thermodynamically favorable manner than conventional precursors for peptide sequencing.

Accordingly, it is an object of this invention to provide novel free radical generators for peptide sequencing.

It is another object of this invention to provide a method for peptide sequencing using the free radical generator.

Other objects and advantages of the present invention will become apparent from the detailed description to follow taken in conjugation with the appended claims and drawings.

DETAILED DESCRIPTION

Figure 1A:
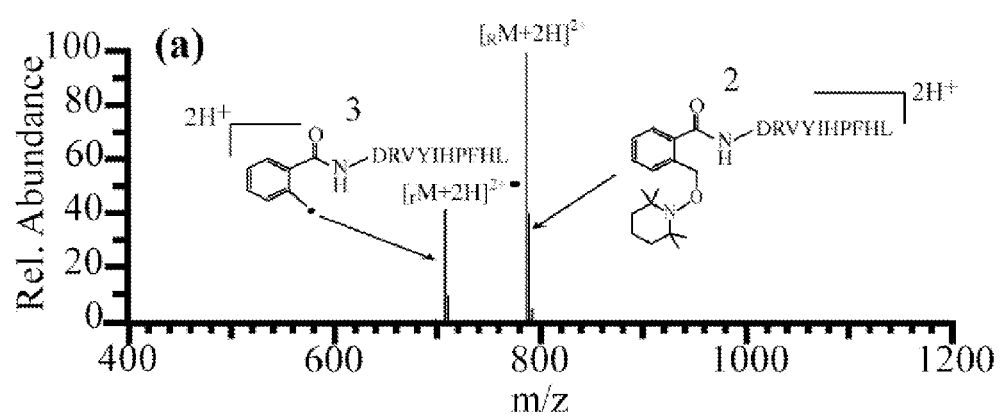
FIG. 1a represents CAD MS/MS spectrum of o-TEMPO-Bz-conjugated Angiotensin I 2+ cations.

In one aspect of the present invention, there is provided a compound represented by the following Formula 1:

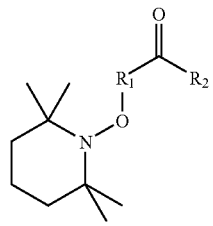

(1)

wherein, $R_1$ is straight or branched $C_{1-10}$ alkyl, unsubstituted or substituted aryl, unsubstituted or substituted heteroaryl or 4-8 membered carbocyclic compound; $R_2$ is hydroxysuccinimide, hydroxysuccinimidyl ester, hydroxyl sulfur-succinimidyl ester, 2,3,4,5,6-pentafluorophenol ester, 4-sulfur-2,3,5,6-tetrafluorophenol ester, acid anhydride, azide, azolide, carboimide, halide, imidazole or imidate.

The present inventors have expand the FRIPS (free radical initiated peptide sequencing) approach by conjugating the N-terminus amino groups or N-terminal amines of lysine side chains to TEMPO-based precursors, providing compounds capable of generating radical species in more thermodynamically favorable manner than conventional precursors for peptide sequencing.

The term used herein "free radical initiated peptide sequencing" refers to a method of sequencing peptides in the gas phase, generally comprising the steps of: (a) conjugating a free radical initiator to the N-terminus of a peptide or protein; (b) electrospraying the conjugated peptide or protein into a mass spectrometer; (c) collisionally activating the conjugated peptide or protein to produce radical species; and (d) performing a second collision to dissociate these radical species to produce fragment ions that are then analyzed by standard techniques such as mass spectrometry for peptide sequencing.

According to a preferred embodiment, $R_1$ is straight or branched $C_{1-5}$ alkyl, unsubstituted aryl, unsubstituted heteroaryl or 4-8 membered carbocyclic compound; $R_2$ is hydroxysuccinimide, hydroxysuccinimidyl ester, hydroxyl sulfur-succinimidyl ester, 2,3,4,5,6-pentafluorophenol ester, 4-sulfur-2,3,5,6-tetrafluorophenol ester, acid anhydride, azide, azolide, carboimide, halide, imidazole or imidate.

Most preferably, the compound of the present invention is represented by the following Formula 2 or 3:

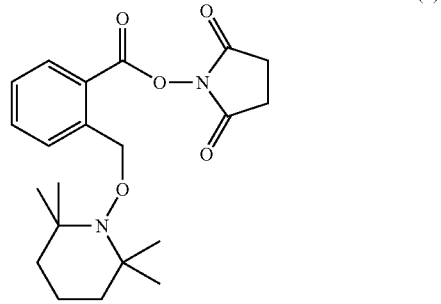

(2)

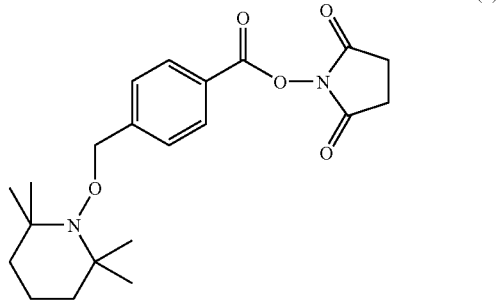

(3)

The term "$C_1$-$C_{10}$ alkyl" is defined herein to be straight chain or branched chain saturated hydrocarbon group from $C_1$ to $C_{10}$, e.g., methyl, ethyl, propyl, isobutyl, pentyl, hexyl, heptyl, octyl, nonyl and decyl.

Afterwards, the peptide conjugated is subject to a primary collision to produce free radical species that are then dissociated by a secondary collision to produce fragment ions.

Ionization is an inevitable step for injecting analytes into a mass spectrometer. The internal energy-transfer condition is the most important in ionization. The ionization of neutral molecules may be performed by electron emission, electron capture, adsorption of hydrogen ions, desorption of hydrogen ions or ions. The ionization may be accomplished according to electron ionization (EI), chemical ionization (CI), fast atom bombardment (FAB), thermospray, electrospray (ESI), atmospheric pressure chemical ionization (APCI) or matrix assisted laser desorption/ionization (MALDI). The analytic method for peptide sequencing includes electron beam, collisionally activated dissociation, infrared multiphoton dissociation and ultraviolet laser radiation.

According to a preferred embodiment, the ions are produced by dissociation of main backbone of peptides. Preferably, the ions may be produced by amino acid side chain fragmentation.

According to a preferred embodiment, fragment ions are selected from the group consisting of a, b, c, x, y, and z-type ions.

The peptide conjugated with the present compound produces a free radical peptide by a primary collision, arising from the homolytic cleavage of bond between the benzyl carbon and the neighboring oxygen of TEMPO. The benzyl radical dissociates H atom of side chains to produce a carbon radical peptide. The radical peptide then undergoes β-fragmentation to cleave the bond between α-carbon and carbonyl carbon, producing a- and x-type ions. The β-fragmentation to cleave the bond between amide nitrogen and α-carbon results in the generation of c- and z-type fragment ions.

The mass analysis of the fragment ions makes it possible to determine the sequence of unknown peptides.

According to a preferred embodiment, the present method is performed in the gas phase.

According to a preferred embodiment, the steps (b)-(d) of the present method are performed on a mass spectrometer.

The mass spectrometer widely used in the field of proteomics generates fragments of high molecular weighted substances such as peptides by electron beam, collisionally activated dissociation, infrared multiphoton dissociation, electron capture dissociation, electron transfer dissociation or ultraviolet laser radiation and analyzes the mass of the fragments to identify the high molecular weighted substance. The mass spectrometer analyzes the ratio of mass to charge (m/z) of substances. The important features of the mass spectrometer include upper mass limit, transmission and resolution. The upper mass limit refers to the highest value in ratios of mass to charge to be determined and the transmission refers to a proportion of ions arrived at a detector from an ion source. The resolution means capability of discriminating two ions having smaller difference in molecular weights with each different signal.

As ion sources are various, the types of mass spectrometer are multitude including quadrupole analyzer, quadrupole ion trap, double-focusing magnetic sector, time-of-flight mass spectrometer (TOFMS) and Fourier transform-ion cyclotron resonance.

The ions are isolated to generate signals that are detected by ion detectors. Exemplary ion detectors include electron multiplier, Faraday cup, array detector and photon multiplier.

According to a preferred embodiment, the peptide comprises a disulfide bond.

The disulfide bond is a covalent linkage formed between two cysteine residues. The sequencing of peptides containing disulfide bonds is considered very difficult since the disulfide bonds are not susceptible to cleavage by general collision activated dissociation procedures. However, the peptide sequencing with the present compound induces the cleavage of disulfide bonds to enable a successful sequencing of peptides.

Compared with diazo or peroxy functionalized precursors, the TEMPO-based precursor of the present invention is chemically more robust and can generate radical species by homolytic cleavage upon thermal activation, enabling sequencing of more various peptides. In addition, the present invention makes it feasible to sequence peptides carrying disulfide bonds.

The present invention will now be described in further detail by examples. It would be obvious to those skilled in the art that these examples are intended to be more concretely illustrative and the scope of the present invention as set forth in the appended claims is not limited to or by the examples.

EXAMPLES

Materials and Methods

Materials

All commercially obtained solvents and reagents were used without further purification except as noted below. Angiotensin I, Angiotensin II, Bradykinine, Interleakin, and Cortistantin-14 were purchased from Sigma. Dry methylene chloride was obtained by distilling from calcium hydride. Analytical thin-layer chromatography (TLC) was carried out on Merck silica gel 60 F254 glass plate and column chromatography was performed on Merck silica gel 60 (70-230 mesh).

$^1$H-NMR and $^{13}$C-NMR spectra were obtained using a Varian Gemini-300 (300 MHz for $^1$H, and 75 MHz for $^{13}$C), or a Varian Inova-500 (500 MHz for $^1$H, and 125 MHz for $^{13}$C) spectrometer. Chemical shifts are reported relative to tetramethylsilane peak (δ 0.00) or solvent peak (δ7.26 for CDCl3 in $^1$H NMR, (δ77.2 for CDCl$_3$ in $^{13}$C NMR). IR spectra were obtained using a Thermo-Nicholet Avartar-330 IR spectrometer with a single-bounce ATR (Ge crystal) accessory (Smart MIRacle). High resolution mass spectra were recorded on a 4.7 Tesla IonSpec ESI-FTMS or on a Micromass LCT ESI-TOF mass spectrometer. Elemental analyses were performed by the Organic Chemistry Research Center at Sogang University using a Carlo Erba EA 1180 elemental analyzer.

Methods

We used compounds containing free radical initiators represented by Formulae 2 and 3. The compounds represented by Formulae 2 and 3 have a TEMPO group at ortho and para position on its benzene ring, respectively. The compounds of Formulae 2 and 3 which are 2-(2,2,6,6-tetramethylpyperidin-1-yloxymethyl)-benzoic acid 2,5-dioxopyrrolidin-1-yl ester and 4-(2,2,6,6-tetramethylpyperidin-1-yloxymethyl)-benzoic acid 2,5-dioxopyrrolidin-1-yl ester, respectively, were synthesized by the inventors. To couple the compound to an amino group of the N-terminus of peptides, a solution of the compound in DMSO was simply mixed with a solution of a peptide of interest in DMSO, and the mixture was allowed to stir for 40 min at room temperature.

(2)

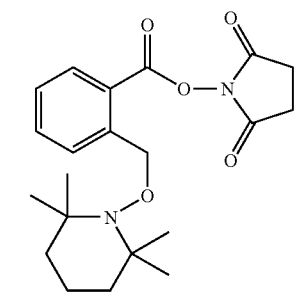

(3)

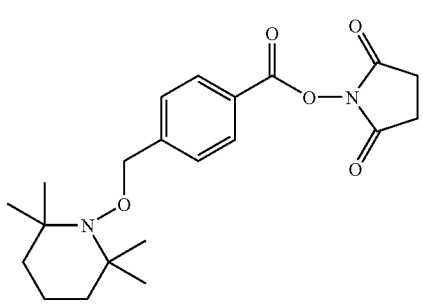

The compound represented by Formula 1 was synthesized according to the following scheme, detail of which is described as follows:

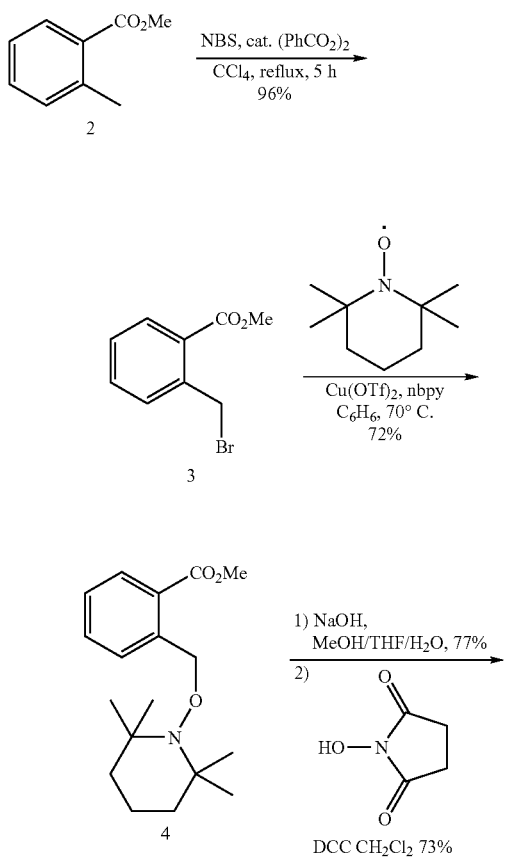

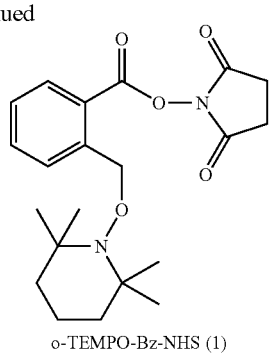

o-TEMPO-Bz-NHS (1)

Synthesis of 2-Methylbenzoic acid methyl ester (4)

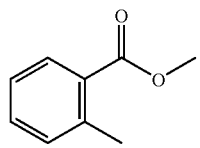

o-Toluic acid (500 mg, 3.67 mmol), dimethyl sulfate (695 mg, 5.51 mmol), and $K_2CO_3$ (558 mg, 4.04 mmol) were placed in a round bottom flask and diluted with acetone (10 mL). After purging the resulting suspension with argon for 5 min, the mixture was heated to reflux for 2 h. The reaction mixture was cooled and concentrated under reduced pressure to remove acetone. After adding water to the mixture, the solution was extracted with ethyl acetate (×3). The combined extracts were washed with brine, dried over anhydrous $MgSO_4$, filtered, and concentrated in vacuo. The crude product was purified by flash chromatography on silica gel (Hex/EtOAc=9:1) to give 2-methylbenzoic acid methyl ester (Formula 4) (415 mg, 75%) as a white solid. $R_f$=0.5 (Hex: EtOAc=9:1); $^1$H NMR (300 MHz, $CDCl_3$): δ 7.91 (dd, J=8.4 and 1.8 Hz, 1H), 7.40 (td, J=7.5 and 1.5 Hz, 1H), 7.24 (m, 2H), 3.89 (s, 3H), 2.60 (s, 3H).

Synthesis of 2-(Bromomethyl)benzoic acid methyl ester (5)

2-Methylbenzoic acid methyl ester (582 mg, 3.88 mmol), N-bromosuccinimid (NBS) (759 mg, 4.26 mmol), and benzoyl peroxide (13 mg, 0.04 mmol) in $CCl_4$ (10 mL) was stirred at reflux for 5 h. After cooling to room temperature, the reaction mixture was extracted with $CH_2Cl_2$ (×3). The extract was washed with brine, dried over anhydrous $MgSO_4$, filtered, and concentrated in vacuo. The crude product was purified by flash chromatography on silica gel (Hex/

EtOAc=9:1) to give 2-(bromomethyl)benzoic acid methyl ester (Formula 5) as a white solid (850 mg, 96%). $R_f$=0.6 (Hex:EtOAc=9:1); $^1$H NMR (300 MHz, CDCl3): δ 7.97 (d, J=7.5 Hz, 1H), 7.48 (m, 2H), 7.38 (td, J=7.8 and 1.2 Hz, 1H), 4.96 (s, 2H), 3.95 (s, 3H). [lit.2 δ 7.97 (m, 1H), 7.40 (m, 3H), 4.96 (s, 2H), 3.95 (s, 3H).

Synthesis of 2-(2,2,6,6-Tetramethylpiperidin-1-yloxymethyl)-benzoic acid methyl ester

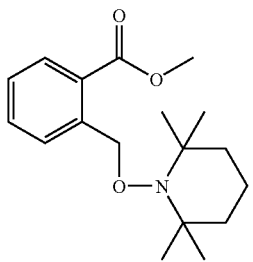

(6)

To a Schlenk flask was added methyl 2-(bromomethyl) benzoate (922 mg, 4.33 mmol), TEMPO (825 mg, 5.28 mmol), Cu(OTf)$_2$ (157 mg, 0.433 mmol), copper powder (275 mg, 4.33 mmol), 4,4'-dinonyl-2,2'-dipyridyl (Nbpy, 708 mg, 1.73 mmol), and benzene (10 mL). The reaction mixture was degassed by argon bubbling for 5 min and heated at 70° C. for 12 h. After cooling the reaction mixture to room temperature, it was filtered through a short pad of silica gel using EtOAc. The filtrate was concentrated in vacuo and the residue was purified by flash column chromatography using Hex:EtOAc (9:1). The desired product (Formula 6) was obtained as a white solid (946 mg, 72%). mp=65° C.; $R_f$=0.7 (Hex: EtOAc=9:1); $^1$H NMR (300 MHz, CDCl$_3$): δ 7.92 (d, J=7.8 Hz, 1H), 7.79 (d, J=7.8 Hz, 1H), 7.54 (t, J=7.8 Hz, 1H), 7.31 (t, j=7.8 Hz, 1H), 5.21 (s, 2H), 3.89 (s, 3H), 1.49 (br s, 4H), 1.37 (br s, 1H), 1.32 (br s, 1H), 1.18 (s, 12H); $^{13}$C NMR (125 MHz, CDCl$_3$) 167.79, 141.21, 132.34, 130.42, 127.79, 127.36, 126.54, 76.69, 60.10, 52.16, 39.89, 33.09, 20.62, 17.34. IR (neat): 2928 (w), 1712 (s), 1467 (w), 1429 (w), 1359 (w), 1271 (s), 1199 (w), 1139 (m), 1089 (w), 1034 (s), 952 (w), 820 (w), 740 (s) cm-1; Anal. Calcd for C21H28N2O5: C. 70.79; H, 8.91; N, 4.59, Found; C. 70.87; H, 8.91; N, 4.49.

Synthesis of 2-(2,2,6,6-Tetramethylpiperidin-1-yloxymethyl)-benzoic acid 2,5-dioxopyrrolidin-1-yl ester (o-TEMPO-Bz-NHS)

2-(2,2,6,6-Tetramethylpiperidin-1-yloxymethyl)-benzoic acid methyl ester (946 mg, 3.1 mmol) was diluted in THF/methanol (1:1, 10 mL). To the solution was added 25% NaOH (aq) (5 mL) at room temperature. After 24 h, the reaction was acidified with 10% HCl and extracted with CH$_2$Cl$_2$ (×3). The combined extracts were washed with brine, dried over anhydrous MgSO$_4$, filtered, and concentrated in vacuo. The crude product was purified by flash chromatography (Hex/EtOAc=1:1) to give 2-(2,2,6,6-tetramethylpiperidin-1-yloxymethyl)-benzoic acid as a white solid (697 mg, 77%). $R_f$=0.6 (Hex:EtOAc=1:1); $^1$H NMR (300 MHz, CDCl3): δ 8.01 (d. J=7.8 Hz, 1H), 7.59 (d, J=7.5 Hz, 1H), 7.53 (t, J=7.2 Hz, 1H), 7.39 (t, J=7.5 Hz, 1H), 5.27 (s, 2H), 1.69-1.46 (br m, 6H), 1.22 (s, 12H): 2-(2,2,6,6-Tetramethylpiperidin-1-yloxymethyl)-benzoic acid (697 mg, 2.39 mmol) and Nhydroxysuccinimid (330 mg, 2.87 mmol) were dissolved in dry CH$_2$Cl$_2$ (10 mL) under argon atmosphere. A solution of N,N'-dicyclohexylcarbodiimide (DCC) (592 mg, 2.87 mmol) was slowly added to the solution at 0° C. After 10 h of stirring, the reaction mixture was filtered through a short pad of silica gel with CH$_2$Cl$_2$ and the filtrate was concentrated to give a crude product. Purification of the crude product by column chromatography on silica gel (Hex:EtOAc=2:1) gave the final product as a white solid (680 mg, 73%). mp=145° C.; Rf=0.5 (Hex:EtOAc=2:1); $^1$H NMR (500 MHz, CDCl3): δ 8.17 (d, J=7.8 Hz, 1H), 7.92 (d, J=7.8 Hz, 1H), 7.68 (t, J=7.8 Hz, 1H), 7.38 (t, J=7.5 Hz, 1H), 5.22 (s, 2H), 2.90 (s, 4H), 1.48 (br s, 4H), 1.36 (br s, 1H), 1.32 (br s. 1H), 1.19 (s, 6H), 1.17 (s, 6H); $^{13}$C NMR (125 MHz, CDCl$_3$) 169.48, 161.45, 143.56, 134.61, 131.29, 127.39, 126.78, 121.73, 76.07, 60.14, 39.86, 33.07, 25.86, 20.64, 17.29; IR (neat): 2932 (w), 1767 (m), 1741 (s), 1468 (w), 1375 (w), 1229 (m), 1207 (s), 1132 (w), 1071 (m), 983 (S), 843 (w), 737 (s), 647 (m) cm-1; Anal. Calcd for C21H28N2O5: C. 64.93; H, 7.27; N, 7.21, Found; C. 64.95; H, 7.15; N, 7.10.

Preparation of Peptide Derivatives

The peptides used, Angiotensin I, Angiotensin II, Bradykinine, Interleakin, and Cortistantin-14 were purchased from Sigma. A solution (100 mM, 100 μL) of 2-(2,2,6,6-tetramethylpyperidin-1-yloxymethyl)-benzoic acid 2,5-dioxopyrrolidin-1-yl ester in DMSO was mixed with a solution (1 mM, 100 μL) of a peptide of interest in DMSO and was allowed to stir for 2 h at room temperature. After removing the solvent under vacuum, the resulting power (peptide derivative) was dissolved in 49:49:2 (v/v/v) solution of methanl:water:acetic acid to obtain a 30 μM solution for electrospray ionization. The solution was subject to electrospray through direct infusion. The direct infusion was carried out at a rate of 3 μL/min using a syringe pump. Mass spectrometry analysis was performed using an ion-trap mass spectrometer (LCQ, Thermo, USA) equipped with MS$^n$ capability. The experimental conditions for sample injection were: spray voltage 5.0-5.5 kV, capillary temperature 140° C., tube lens offset voltage 0 kV. MS/MS and MS$^3$ analysis using collisionally activated dissociation (CAD) was performed using 'Advanced scan function' of the mass spectrometer. After sample injection and isolation of ions desired through a mass selection procedure, the ions were subjected to collision to helium gas. The ions isolated had ±5-7 Da and the collision energy was adjusted to 18-20%. The collisionally activated dissociation procedure was performed twice for peptide fragmentation. The radical initiator was dissociated during the first collision for activating peptides to radical peptides in hole-electron state. The radical peptide ions were selectively isolated under vacuum and then their backbones were fragmented by the second collision.

Results

Figure is represents the MS/MS mass spectrum for o-TEMPO-Bz-conjugated Angiotensin I 2+ cations at m/z 785.9, 2. Ortho-TEMPO-Bz-Angiotensin I conjugated ions yielded the fragment (M-156)2+ as the major product upon collisional activation, which is a free radical ion species 3 arising from the homolytic cleavage of the bond between the benzyl carbon and the neighboring oxygen in 2. The formed radical ion species at m/z 707.6 was isolated in the mass spectrometer and subjected to the subsequent CAD.

Figure 1B:
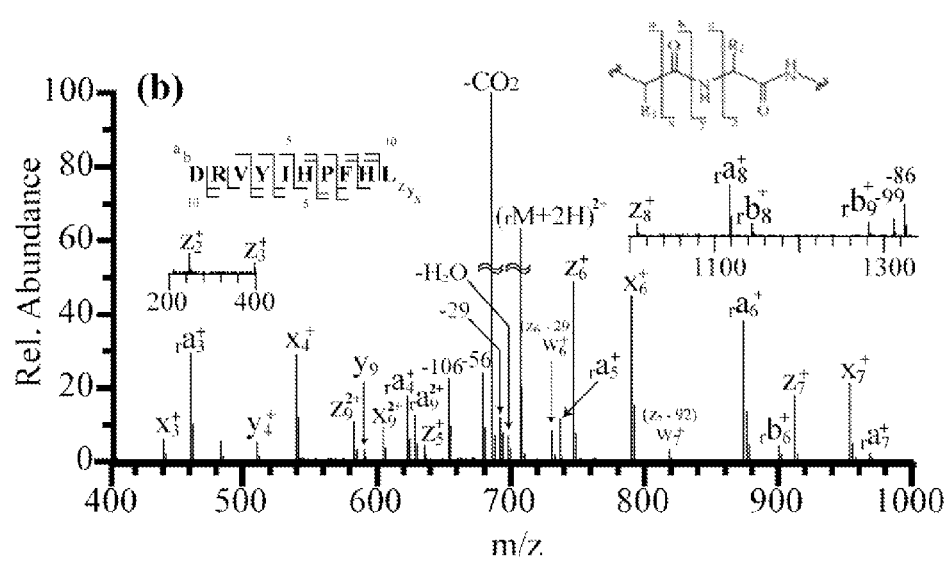
FIG. 1b represents $MS^3$ spectrum for ortho-TEMPO-Bz conjugated Angiotensin I 2+ cations. The subscript 'r' in the left side of fragment ion types, for example, $_ra_3^+$, indicates that the radical part $.CH_2C_6H_4CO$— is attached to the ion.

FIG. 1b shows the resulting product spectrum for ortho-TEMPO-Bz-conjugated radical ions. Here, a, x, z type ions were the major fragment ions, and b and y ions were the minor fragments. Also of note, numerous neutral loss peaks were observed, including the loss of H$_2$O (−18 Da), CO$_2$ (−44 Da), and side chains of tyrosine (−106 Da), arginine (−86, 99 Da), leucine (−56 Da), and isoleucine (−29 Da). Side chain neutral losses from radical cations are reported to occur often. In particular, the side chain loss from leucine and isoleucine is expected to be very useful since it allows the distinction of these isobaric residues.

Figure 2:
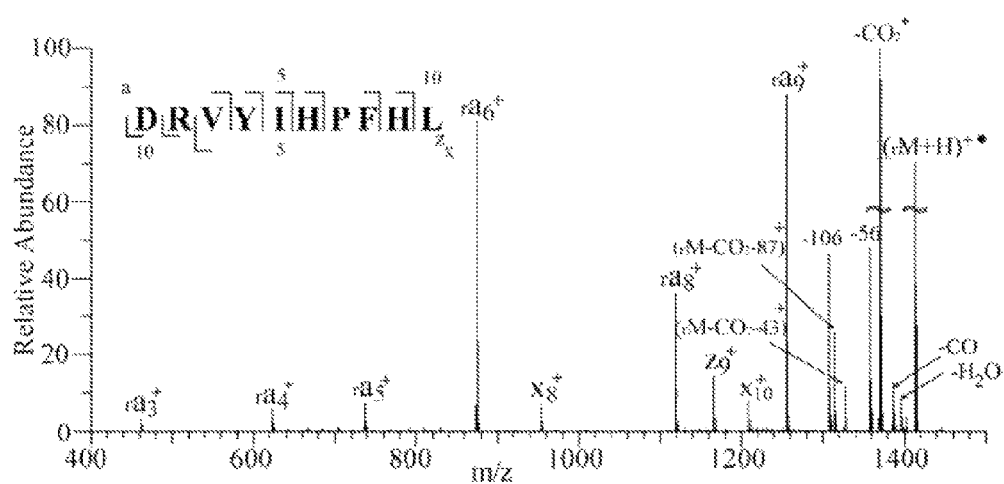
FIG. 2 represents $MS^3$ spectrum of ortho-TEMPO-conjugated Angiotension I 1+ ions.

The same FRIPS approach was also taken for o-TEMPO-Bz conjugated Angiotensin 1+ cations (FIG. 2). Singly protonated conjugated peptide ions were also susceptible to extensive backbone cleavages and some neutral losses, although a fewer number of fragment ions were observed, compared with the 2+ conjugated peptides ions, due to the lack of the extra proton charge. Most of the detected fragment ions were a-type ions, primarily due to the presence of the most basic arginine residue in the N-terminal region of Angiotensin I. For comparison, CAD and ECD mass spectra were also obtained, and their fragmentation patterns differed markedly from that of TEMPO-FRIPS (data not shown), consistent with the results from the Beauchamp group.

Figure 3:
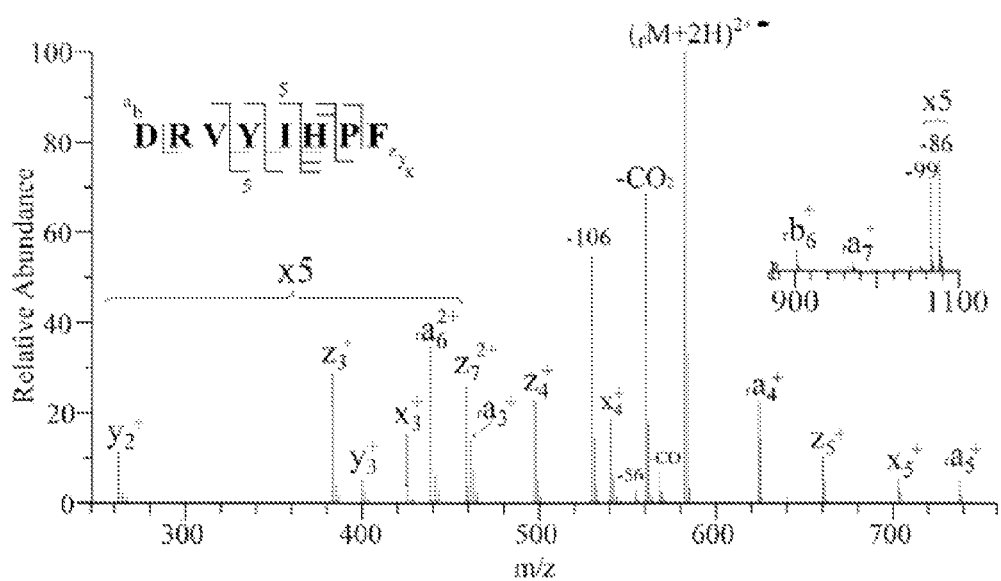
FIG. 3 represents $MS^3$ spectrum of ortho-TEMPO-conjugated Angiotension II 2+ ions.
Figure 4:
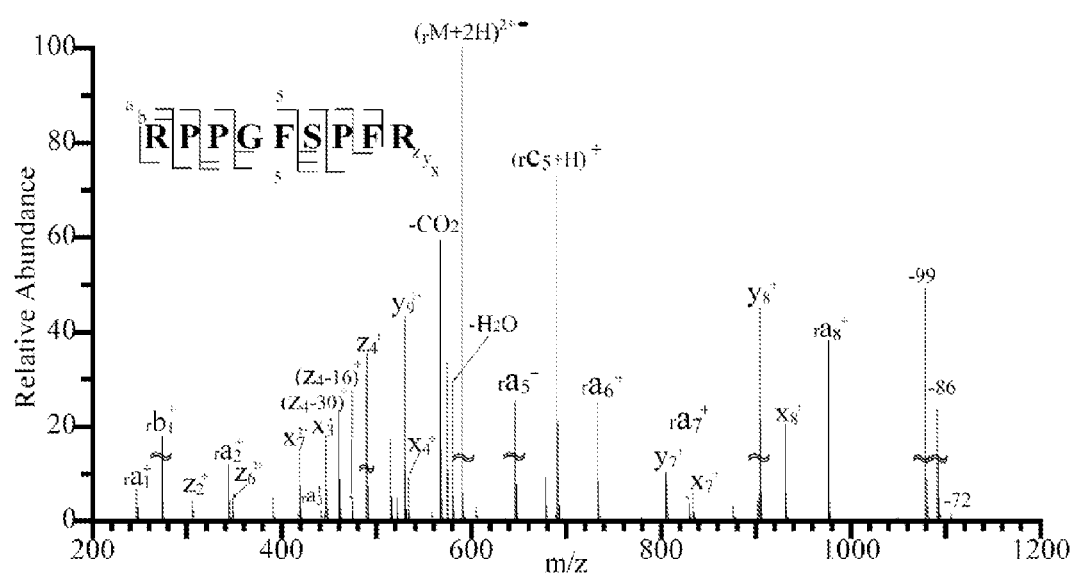
FIG. 4 represents $MS^3$ spectrum of ortho-TEMPO-conjugated Bradykinin 2+ ions.
Figure 5:
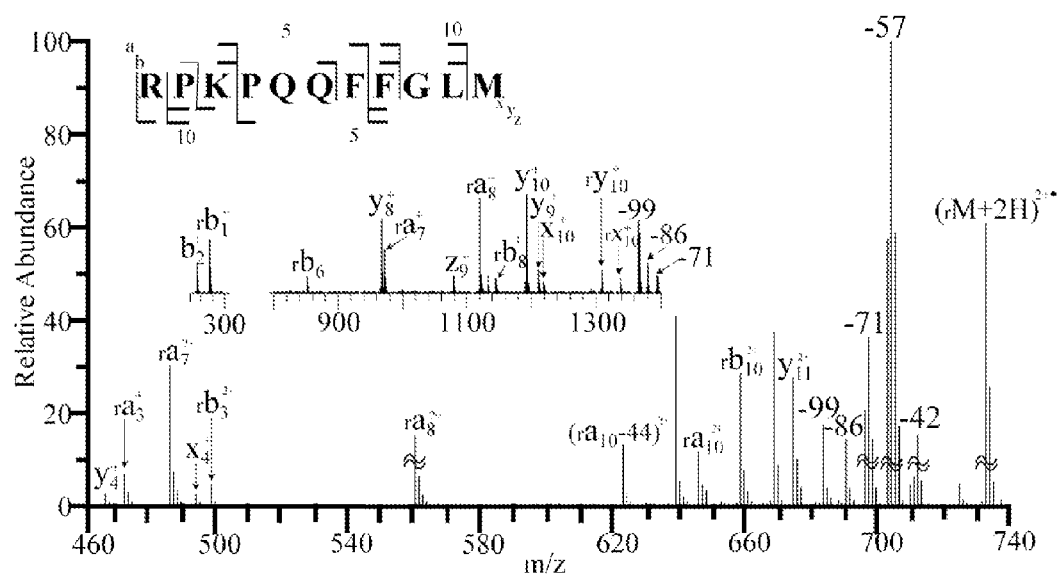
FIG. 5 represents $MS^3$ spectrum of ortho-TEMPO-Bz-conjugated Substance P 2+ peptide ions. Backbone fragmentations are summarized in the inset. Neutral losses such as –42, –57, –71, –86, and –99 Da are derived from Arg side chain.
Figure 6:
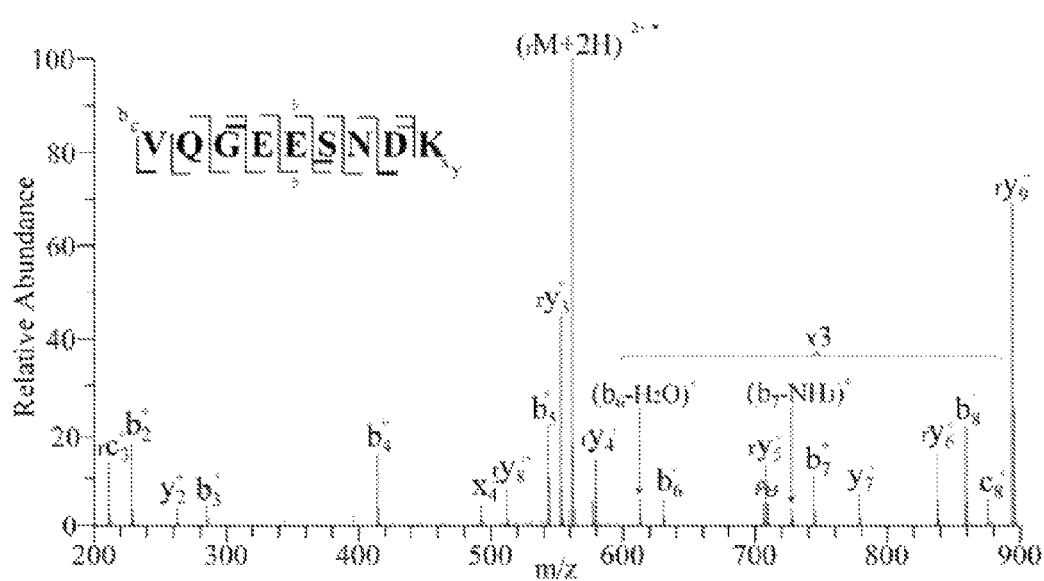
FIG. 6 represents $MS^3$ spectrum of ortho-TEMPO-conjugated Interleakin 2+ ions.

TEMPO-FRIPS experiments were also conducted for other peptides. Results for peptides that do not contain any lysine were very similar to those of Angiotensin I (see FIGS. 3 and 4). However, a lysine side chain could be modified as well. For example, as shown in FIG. 5, $MS^3$ on the o-TEMPO-Bz-conjugated Substance P 2+ ions demonstrated that some of the fragments resulted from the molecular ions in which o-TEMPO-Bz group was attached to the ε-amino group of a lysine side chain, such as $b_2^+$, $_rx_{10}^+$, and $_ry_{10}^+$. For an Interleakin peptide (9-mer) that has a lysine residue in the C-terminus, the o-TEMPO-Bz group attached more frequently to the lysine side chain amino group than to the N-terminus (FIG. 6). Further experiments are underway to better characterize this phenomenon.

Figure 7:
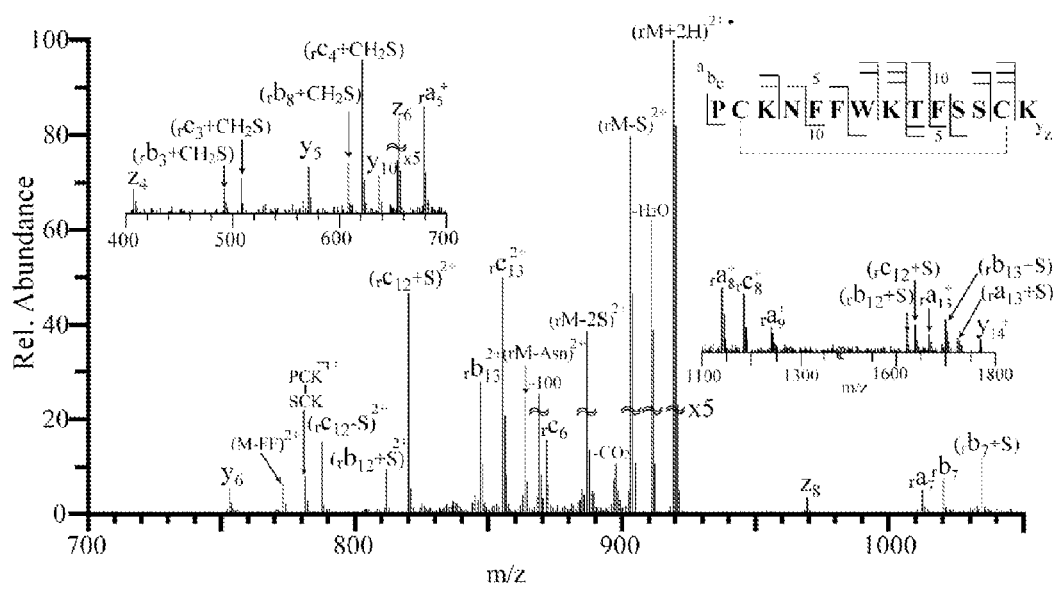
FIG. 7 represents $MS^3$ spectrum of ortho-TEMPO-Bz-conjugated Cortistantin-14 2+ peptide ions. Backbone fragmentations are summarized in the inset. (the disulfide bond between two cysteine residues is denoted with a dotted line, which forms a loop).

To determine how a disulfide bond between two cysteine residues responds to the TEMPO-FRIPS method, o-TEMPOBz-conjugated Cortistantin-14 peptide, which contains a disulfide bond, was subjected to $MS^3$. Disulfide bond cleavage is rarely observed in other slow heating $MS^n$ methods. As shown in FIG. 7, TEMPO-FRIPS induced cleavage of the disulfide bond in addition to the peptide backbone bonds. Most product ions in FIG. 7 resulted from multiple backbone fragmentations in a loop region with the disulfide bond intact or a combination of a single backbone fragmentation in a loop region and the disulfide bond cleavage at either S—S or at C—S. A C—C bond neighboring the S—S bond in the side chain of cysteine was also cleaved as denoted, for example, ($_rc_3+CH_2S$) in FIG. 7. The disulfide bond cleavage in TEMPO-FRIPS is in agreement with ECD results. It is also of note that the disulfide bond was inert to $MS^3$ application for perm/carbonate-modified peptides.

Figure 8:
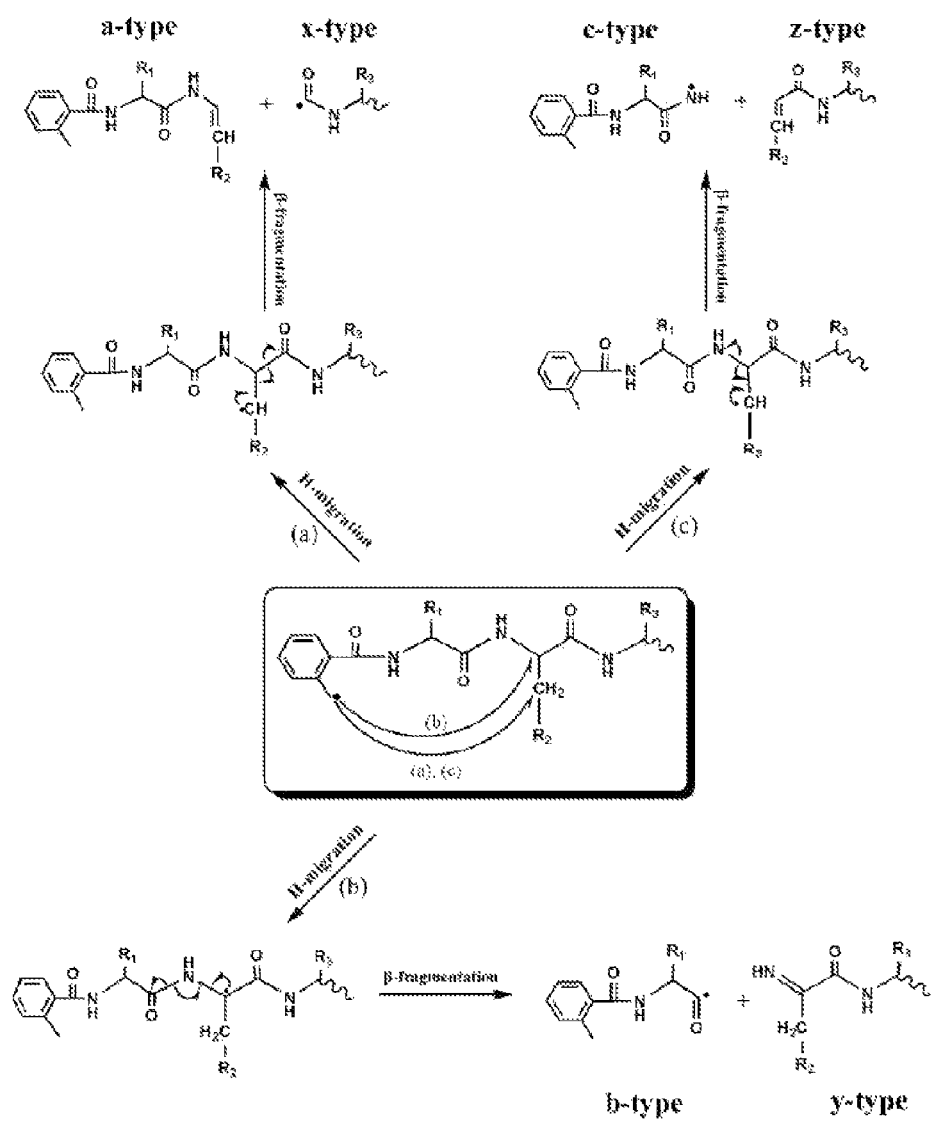
FIG. 8 schematically represents suggested mechanism of TEMPO-FRIPS peptide backbone dissociation.

A mechanism for FRIPS was previously suggested (FIG. 8). To generate a, c, x, and z ions, a hydrogen atom is initially abstracted from a methylene group of the amino acid side chains attached to an α-carbon. The formed carbon-centered radical then undergoes β-fragmentation to result in a/x or c/z complementary-pair ions. In this mechanism, the homolytic bond cleavage of a C—H bond may play an important role in determining the dissociation pathways. As indicated by Hodyss et al., calculations suggested that the α-carbon hydrogens in the peptide backbone are less strongly bound compared to methylene hydrogens. However, abstraction of the α-carbon hydrogens, which instead lead to b, y ions, can not explain the dominant occurrence of a/x or c/z ions observed in Vazo 68 and TEMPO-FRIPS experiments. To explain this contradictory result, other factors such as secondary structure was suggested to influence the relative homolytic bond dissociation energy. To verify this supposition, we compared the dissociation behavior of ortho- and para-TEMPO-Bz conjugated peptides. Despite our expectation that the different radical positions in the benzene ring may impose some structural effect in the hydrogen-abstraction step, our preliminary results for ortho- and para-TEMPO-Bz conjugated peptides were not significantly different.

As demonstrated above, TEMPO-FRIPS has many useful fragmentation characteristics and is very similar to ECD/ETD and other radical-driven fragmentation methods such as Vazo 68, peroxycarbamates-conjugated, and divalent transition metal-complexed peptides $MS^3$. The FRIPS approach has the advantage of universality, as it can be used in any type of a tandem mass spectrometer. The FRIPS approach should provide a good complementary tool for peptide gas phase sequencing.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:
1. A method for peptide sequencing, comprising the steps of:
   (a) conjugating a compound represented by the following Formula 1A or Formula 1B with a peptide to form a conjugated peptide:

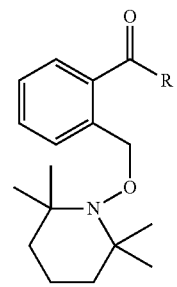

(1A)

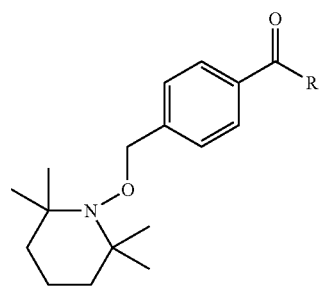

(1B)

wherein
R is 2,5-dioxo-1-pyrrolidinyloxy, 2,3,4,5,6-pentafluorophenoxy, 4-sulfur-2,3,5,6-tetrafluorophenoxy, halide, or azide;

(b) producing molecular fragments containing at least one free radical species by activating the conjugated peptide through a primary collision in a mass spectrometer;

(c) producing fragment ions by dissociating the molecular fragments through a secondary collision in a mass spectrometer; and (d) analyzing the mass of the fragment ions.

2. The method according to claim 1, wherein the compound is conjugated with an amino group of the N-terminal of the peptide or with an amine group of a lysine residue of the peptide.

3. The method according to claim 1, wherein the fragment ions are produced by amino acid side chain fragmentation.

4. The method according to claim 1, wherein the fragment ions are selected from the group consisting of a, b, c, x, y, and z-type ions.

5. The method according to claim 1, wherein the method is performed in the gas phase.

6. The method according to claim 1, wherein the steps (b)-(d) are performed on a mass spectrometer.

7. The method according to claim 1, wherein the peptide comprises a disulfide bond.

8. The method according to claim 1, wherein the compound is represented by the following Formula 2 or 3:

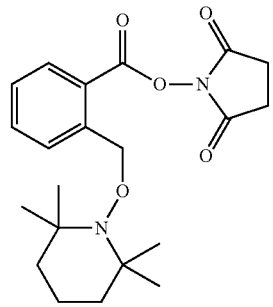
(2)

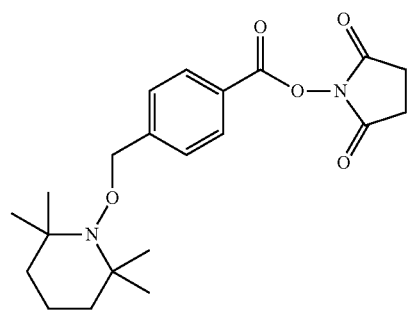
(3)

* * * * *